United States Patent
Pennell et al.

(10) Patent No.: US 9,133,124 B2
(45) Date of Patent: Sep. 15, 2015

(54) CRYSTALLINE FORM OF THE SODIUM SALT OF 4-TERT-BUTYL-N-[4-CHLORO-2-(1-OXY-PYRIDINE-4-CARBONYL)-PHENYL]-BENZENESULFONAMIDE

(75) Inventors: Andrew M. K. Pennell, San Francisco, CA (US); Solomon Ungashe, Fremont, CA (US)

(73) Assignee: ChemoCentryx, Inc., Mountain View, CA (US)

( * ) Notice: Subject to any disclaimer, the term of this patent is extended or adjusted under 35 U.S.C. 154(b) by 172 days.

(21) Appl. No.: 13/554,169

(22) Filed: Jul. 20, 2012
(Under 37 CFR 1.47)

(65) Prior Publication Data

US 2013/0059893 A1    Mar. 7, 2013

Related U.S. Application Data

(60) Provisional application No. 61/510,832, filed on Jul. 22, 2011.

(51) Int. Cl.
*C07D 213/50* (2006.01)
*A61K 31/44* (2006.01)
*C07D 213/89* (2006.01)

(52) U.S. Cl.
CPC .................................. *C07D 213/89* (2013.01)

(58) Field of Classification Search
IPC ....................................................... C07D 213/50
See application file for complete search history.

(56) References Cited

FOREIGN PATENT DOCUMENTS

WO    WO 2004/046092 A2    6/2004

OTHER PUBLICATIONS

Hydrate Lab, URL: http://www.chalkbored.com/lessons/chemistry-11/hydrate-lab.pdf. Accessed online May 17, 2008.*

* cited by examiner

*Primary Examiner* — Michael Barker
*Assistant Examiner* — Po-Chih Chen
(74) *Attorney, Agent, or Firm* — Brinks Gilson & Lione; Ryan L. Marshall (57) ABSTRACT

A novel crystalline form of the sodium salt of 4-tert-butyl-N-[4-chloro-2-(1-oxy -pyridine-4-carbonyl)-phenyl]-benzenesulfonamide and pharmaceutical compositions containing the same are disclosed. Processes for the preparation thereof and methods for use thereof are also disclosed.

17 Claims, 10 Drawing Sheets

CRYSTALLINE FORM OF THE SODIUM SALT OF 4-TERT-BUTYL-N-[4-CHLORO-2-(1-OXY-PYRIDINE-4-CARBONYL)-PHENYL]-BENZENESULFONAMIDE

RELATED APPLICATIONS

This application claims the benefit of U.S. Provisional Application No. 61/510,832, filed on Jul. 22, 2011, the disclosure of which is incorporated herein by reference in its entirety.

BACKGROUND OF THE INVENTION

In the pursuit of a developable form of a solid, orally-administered pharmaceutical compound, a number of specific features are sought. Although an amorphous form of a pharmaceutical compound may be developed, compounds having high crystallinity are generally preferred. Often such highly crystalline compounds are salts.

International Publication Number WO 2004/046092 describes a series of compounds which are indicated as antagonists of the CCR9 receptor, and which are indicated as being useful in the treatment of CCR9-mediated disorders. Specifically disclosed in that application is the compound 4-tert-butyl-N-[4-chloro-2-(1-oxy-pyridine-4-carbonyl)-phenyl]-benzenesulfonamide (hereinafter "Compound A"). Identification of a stable, crystalline form of such compound with suitable properties for oral administration would be highly desirable for the treatment of CCR9-mediated diseases.

SUMMARY OF THE INVENTION

The present invention relates to a novel crystalline form of the sodium salt of 4-tert-butyl-N-[4-chloro-2-(1-oxy-pyridine-4-carbonyl)-phenyl]-benzenesulfonamide (hereinafter "Compound B"). The compound of the invention is represented by Structure (I):

(I)

The compound of this invention is useful for antagonizing the CCR9 receptor, and for treating diseases such as inflammatory bowel disease, including Crohn's disease and ulcerative colitis.

DETAILED DESCRIPTION OF THE INVENTION

The present invention is directed to a crystalline form of the sodium salt of 4-tert-butyl-N-[4-chloro-2-(1-oxy-pyridine-4-carbonyl)-phenyl]-benzenesulfonamide (hereinafter "Compound B—crystalline form").

In some embodiments, Compound B—crystalline form is anhydrous (hereinafter "Compound B—anhydrous crystalline form").

In some embodiments, Compound B—anhydrous crystalline form is characterized by an X-ray powder diffraction (XRPD) pattern comprising at least three diffraction angles, when measured using Cu $K_\alpha$ radiation, selected from a group consisting of about 4.7, 9.1, 12.0, 14.2, 17.7, 18.1, 19.2, 19.8, 20.1, 21.3, 22.5, 24.3, 27.0, 27.2, 27.7, 28.6, 28.8, 29.0, 30.1, 31.6, 33.5, 33.6, and 37.6 degrees 2θ. In one embodiment, Compound B—anhydrous crystalline form is characterized by an X-ray powder diffraction (XRPD) pattern comprising at least three diffraction angles, when measured using Cu $K_\alpha$ radiation, selected from a group consisting of about 4.7, 9.1, 12.0, 14.2, 18.1, 19.2, 19.8, 20.1, 21.3, 22.5, 24.3, 27.2, 28.8, and 37.6 degrees 2θ. In another embodiment, Compound B—anhydrous crystalline form is characterized by an X-ray powder diffraction (XRPD) pattern comprising at least three diffraction angles, when measured using Cu $K_\alpha$ radiation, selected from a group consisting of about 4.7, 12.0, 14.2, 18.1, 19.2, and 24.3 degrees 2θ. In still another embodiment, Compound B—anhydrous crystalline form is characterized by an X-ray powder diffraction (XRPD) pattern comprising diffraction angles, when measured using Cu $K_\alpha$ radiation, of about 4.7, 12.0, 14.2, 18.1, 19.2, and 24.3 degrees 2θ. In still another embodiment, Compound B—anhydrous crystalline form is characterized by an X-ray powder diffraction (XRPD) pattern comprising diffraction angles, when measured using Cu $K_\alpha$ radiation, of about 4.7, 12.0, and 19.2 degrees 2θ. In still another embodiment, Compound B—anhydrous crystalline form is characterized by an X-ray powder diffraction (XRPD) pattern comprising diffraction angles, when measured using Cu $K_\alpha$ radiation, of about 4.7, 12.0, 18.1, and 19.2 degrees 2θ. In still another embodiment, Compound B—anhydrous crystalline form is characterized by an X-ray powder diffraction (XRPD) pattern comprising diffraction angles, when measured using Cu $K_\alpha$ radiation, of about 4.7, 12.0, 14.2, 18.1, and 19.2 degrees 2θ. In still another embodiment, Compound B—anhydrous crystalline form is characterized by an X-ray powder diffraction (XRPD) pattern comprising diffraction angles, when measured using Cu $K_\alpha$ radiation, of about 4.7, 12.0, 19.2, and 24.3 degrees 2θ. In still another embodiment, Compound B—anhydrous crystalline form is characterized by an X-ray powder diffraction (XRPD) pattern comprising diffraction angles, when measured using Cu $K_\alpha$ radiation, of about 4.7, 12.0, 18.1, 19.2, and 24.3 degrees 2θ. In still another embodiment, Compound B—anhydrous crystalline form is characterized by an X-ray powder diffraction (XRPD) pattern comprising diffraction angles, when measured using Cu $K_\alpha$ radiation, of about 4.7, 19.2, and 24.3 degrees 2θ. In still another embodiment, Compound B—anhydrous crystalline form is characterized by an X-ray powder diffraction (XRPD) pattern comprising diffraction angles, when measured using Cu $K_\alpha$ radiation, of about 12.0, 19.2, and 24.3 degrees 2θ. In yet another embodiment, Compound B——anhydrous crystalline form is characterized by an X-ray powder diffraction (XRPD) pattern substantially in accordance with FIG. 3.

In other embodiments, Compound B—anhydrous crystalline form is characterized by a Raman spectrum comprising at least three peaks at positions selected from a group consisting of peaks at about 601, 632, 651, 664, 726, 740, 803, 853, 931, 1080, 1123, 1138, 1162, 1318, 1395, 1458, 1526, 1595, 1614, and 1647 $cm^{-1}$. In one embodiment, Compound B——anhydrous crystalline form is characterized by a Raman spectrum comprising at least three peaks at positions selected from a group consisting of peaks at about 664, 740, 803, 853, 1080, 1123, 1162, 1318, 1458, 1526, 1595, 1614, and 1647 $cm^{-1}$. In another embodiment, Compound B—anhydrous crystalline form is characterized by a Raman spectrum comprising at least three peaks at positions selected from a group consisting of peaks at about 664, 1162, 1458, 1614, and 1647 $cm^{-1}$. In still another embodiment, Compound B—anhydrous crystalline form is characterized by a Raman spectrum comprising peaks at about 664, 740, 803, 853, 1080, 1123, 1162, 1318, 1458, 1526, 1595, 1614, and 1647 $cm^{-1}$. In yet another embodiment, Compound B—anhydrous crystalline form is characterized by a Raman spectrum substantially in accordance with FIG. 6.

Figure 8:
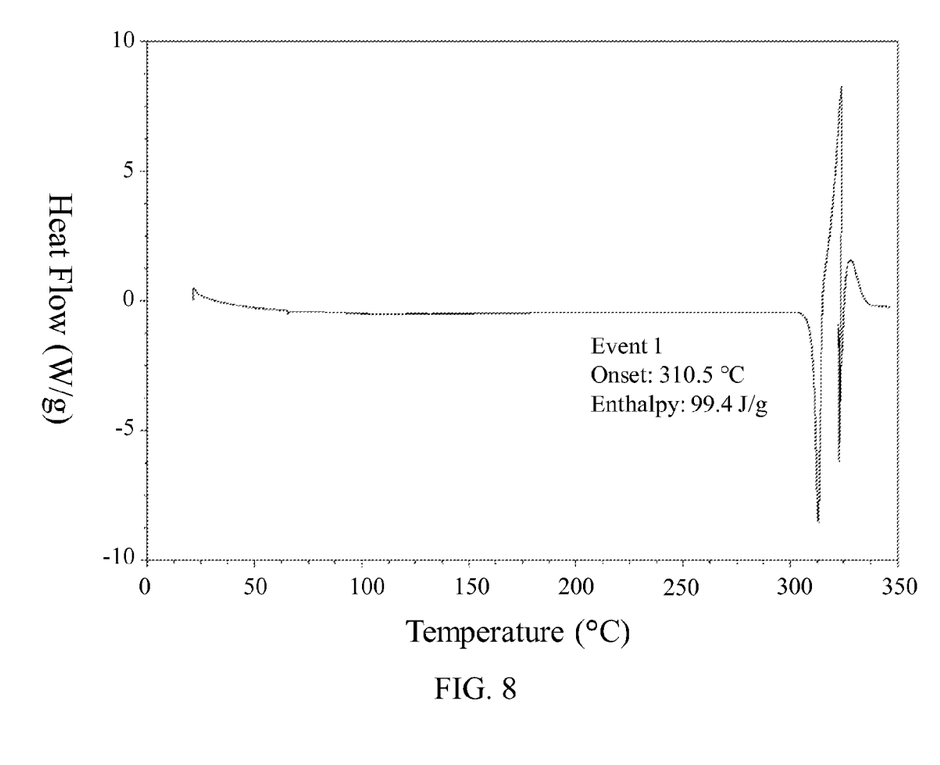
FIG. 8 shows a differential scanning calorimetry trace of Compound B—anhydrous crystalline form.
Figure 10:
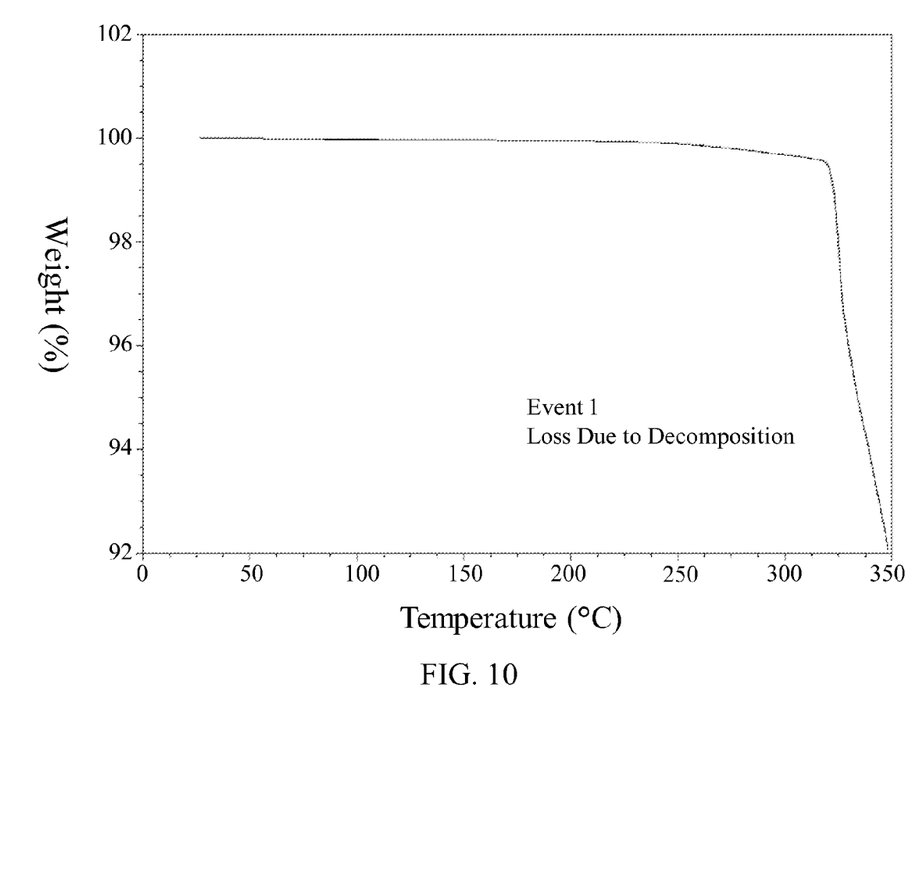
FIG. 10 shows a thermogravimetric analysis trace of Compound B—anhydrous crystalline form.

In further embodiments, Compound B—anhydrous crystalline form is characterized by a differential scanning calorimetry trace substantially in accordance with FIG. 8 and/or a thermogravimetric analysis trace substantially in accordance with FIG. 10.

In still further embodiments, as a person having ordinary skill in the art will understand, Compound B—anhydrous crystalline form is characterized by any combination of the analytical data characterizing the aforementioned embodiments.

Figure 1:
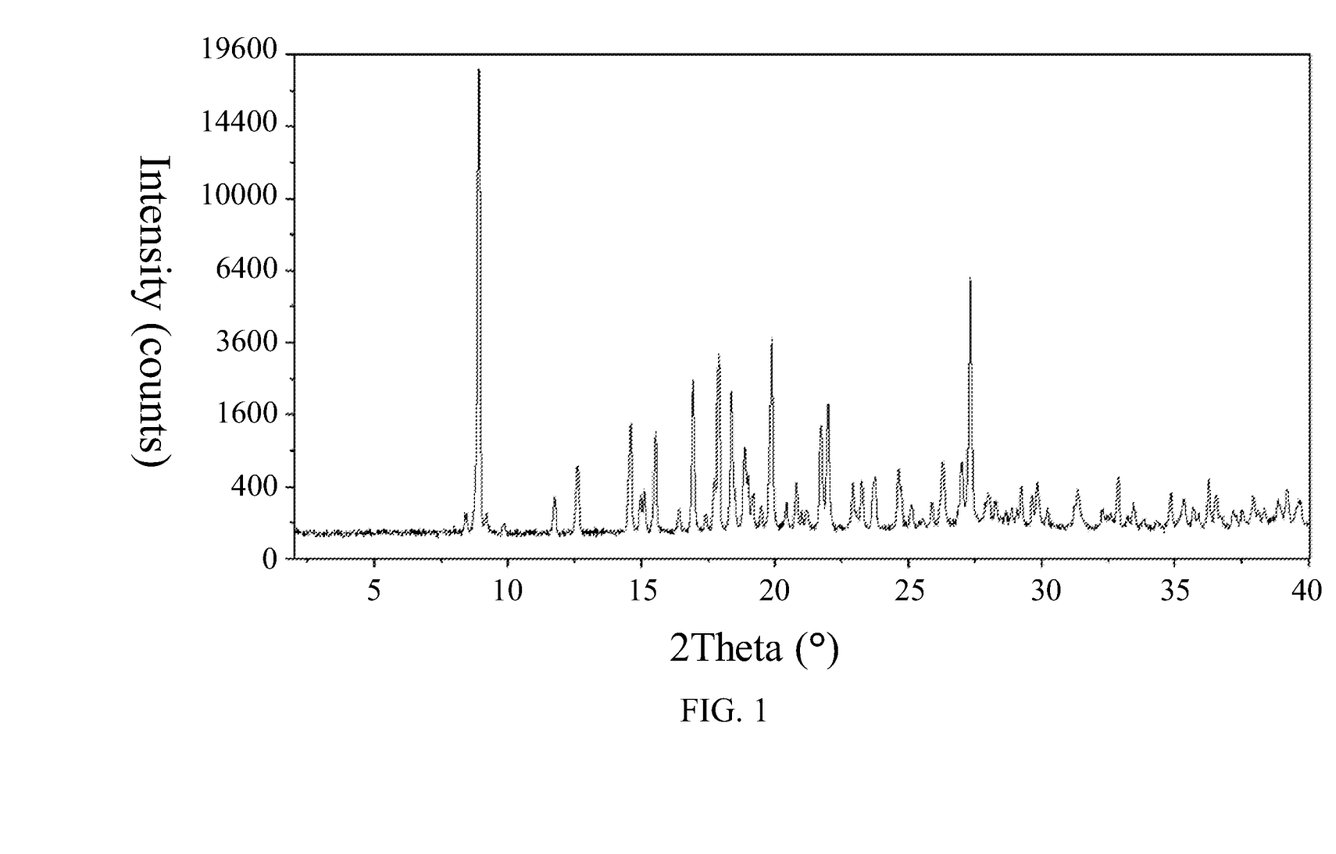
FIG. 1 shows an X-ray powder diffraction pattern of Compound A.
Figure 2:
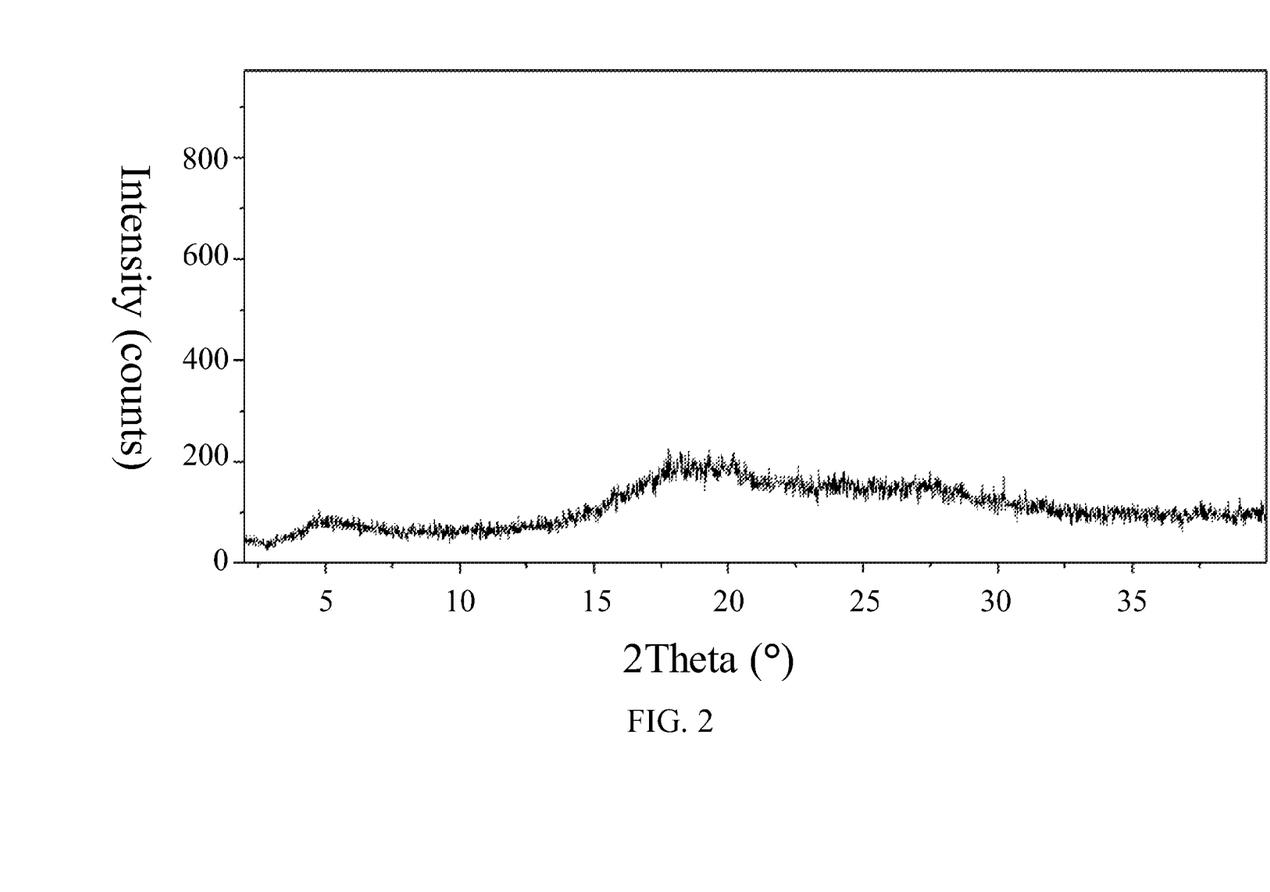
FIG. 2 shows an X-ray powder diffraction pattern of Compound B—amorphous form.
Figure 3:
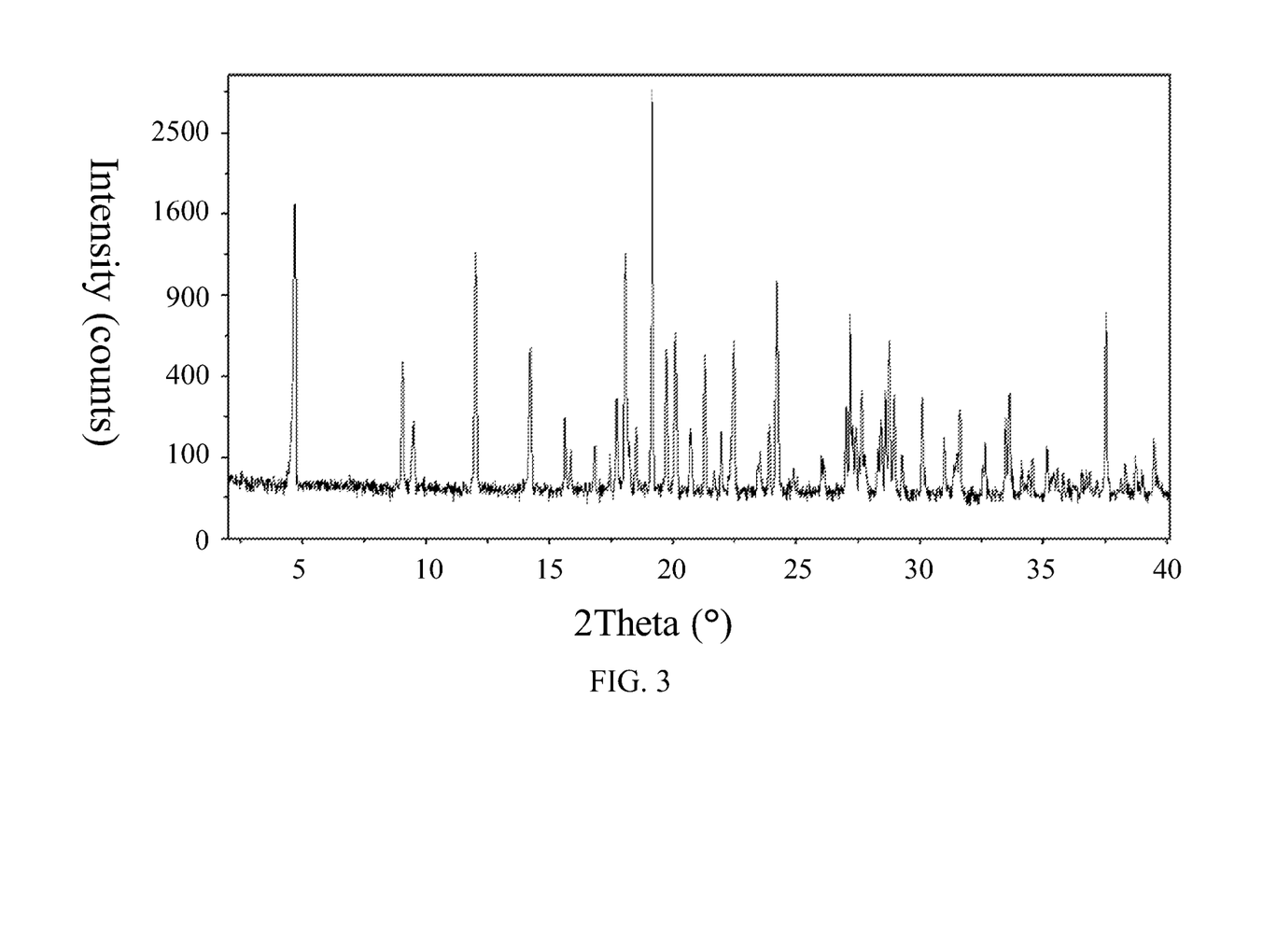
FIG. 3 shows an X-ray powder diffraction pattern of Compound B—anhydrous crystalline form.

An XRPD pattern will be understood to comprise a diffraction angle (expressed in degrees 2θ) of "about" a value specified herein when the XRPD pattern comprises a diffraction angle within ±0.2 degrees 2θ of the specified value. Further, it is well known and understood to those skilled in the art that the apparatus employed, humidity, temperature, orientation of the powder crystals, and other parameters involved in obtaining an X-ray powder diffraction (XRPD) pattern may cause some variability in the appearance, intensities, and positions of the lines in the diffraction pattern. An X-ray powder diffraction pattern that is "substantially in accordance" with that of FIG. 1, 2, or 3 provided herein is an XRPD pattern that would be considered by one skilled in the art to represent a compound possessing the same crystal form as the compound that provided the XRPD pattern of FIG. 1, 2, or 3. That is, the XRPD pattern may be identical to that of FIG. 1, 2, or 3, or more likely it may be somewhat different. Such an XRPD pattern may not necessarily show each of the lines of any one of the diffraction patterns presented herein, and/or may show a slight change in appearance, intensity, or a shift in position of said lines resulting from differences in the conditions involved in obtaining the data. A person skilled in the art is capable of determining if a sample of a crystalline compound has the same form as, or a different form from, a form disclosed herein by comparison of their XRPD patterns. For example, one skilled in the art can overlay an XRPD pattern of a sample of the sodium salt of 4-tert-butyl-N-[4-chloro-2-(1-oxy-pyridine-4-carbonyl)-phenyl]-benzenesulfonamide, with FIG. 3 and, using expertise and knowledge in the art, readily determine whether the XRPD pattern of the sample is substantially in accordance with the XRPD pattern of Compound B—anhydrous crystalline form. If the XRPD pattern is substantially in accordance with FIG. 3, the sample form can be readily and accurately identified as having the same form as Compound B—anhydrous crystalline form.

Figure 4:
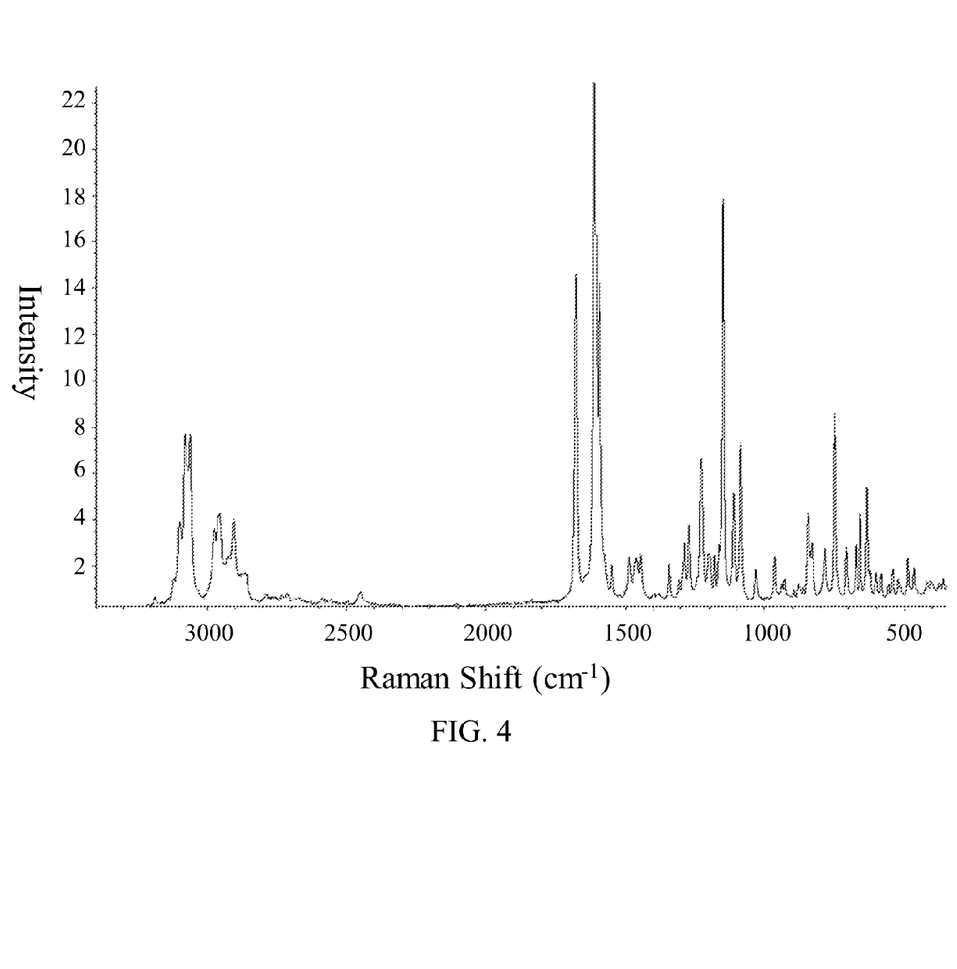
FIG. 4 shows a Raman spectrum of Compound A.
Figure 6:
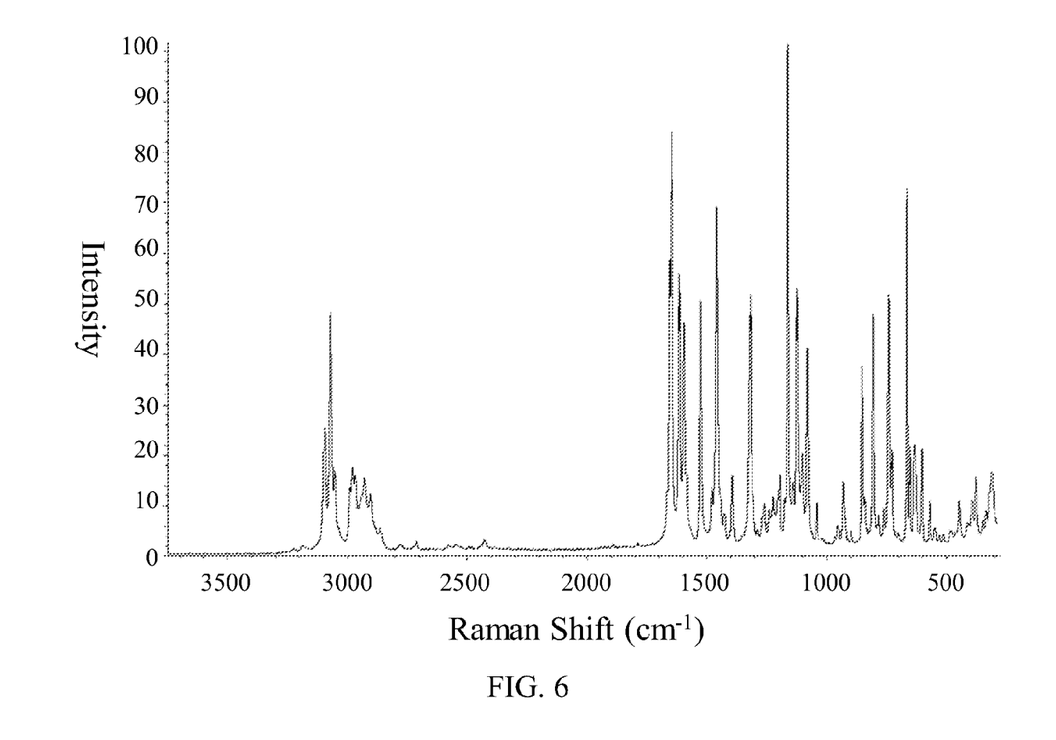
FIG. 6 shows a Raman spectrum of Compound B—anhydrous crystalline form.

A Raman spectrum will be understood to comprise a peak (expressed in $cm^{-1}$) of "about" a value specified herein when the Raman spectrum comprises a peak within ±4.0 $cm^{-1}$ of the specified value. Further, it is also well known and understood to those skilled in the art that the apparatus employed, humidity, temperature, orientation of the powder crystals, and other parameters involved in obtaining a Raman spectrum may cause some variability in the appearance, intensities, and positions of the peaks in the spectrum. A Raman spectrum that is "substantially in accordance" with that of FIG. 4 or 6 provided herein is a Raman spectrum that would be considered by one skilled in the art to represent a compound possessing the same crystal form as the compound that provided the Raman spectrum of FIG. 4 or 6. That is, the Raman spectrum may be identical to that of FIG. 4 or 6, or more likely it may be somewhat different. Such a Raman spectrum may not necessarily show each of the peaks of any one of the spectra presented herein, and/or may show a slight change in appearance, intensity, or a shift in position of said peaks resulting from differences in the conditions involved in obtaining the data. A person skilled in the art is capable of determining if a sample of a crystalline compound has the same form as, or a different form from, a form disclosed herein by comparison of their Raman spectra. For example, one skilled in the art can overlay a Raman spectrum of a sample of the sodium salt of 4-tert-butyl-N-[4-chloro-2-(1-oxy-pyridine-4-carbonyl)-phenyl]-benzenesulfonamide, with FIG. 6 and, using expertise and knowledge in the art, readily determine whether the Raman spectrum of the sample is substantially in accordance with the Raman spectrum of Compound B—anhydrous crystalline form. If the Raman spectrum is substantially in accordance with FIG. 6, the sample form can be readily and accurately identified as having the same form as Compound B—anhydrous crystalline form.

"The compound of the invention" means the sodium salt of 4-tert-butyl-N-[4-chloro-2-(1-oxy-pyridine-4-carbonyl)-phenyl]-benzenesulfonamide, specifically the crystalline form defined herein as Compound B—crystalline form, or in some embodiments, Compound B—anhydrous crystalline form.

The invention includes a therapeutic method for treating or ameliorating a CCR9-mediated disorder in a subject in need thereof comprising administering to a subject in need thereof an effective amount of the compound of the invention or a composition comprising an effective amount of the compound of the invention and an optional pharmaceutically acceptable carrier. The invention further includes the compound of the invention for use in therapy, the compound of the invention for use in treating a CCR9-mediated disorder, and the compound of the invention for use in treating an inflammatory bowel disease.

As used herein, the phrase "CCR9-mediated disorder" and related phrases and terms refer to a condition or disease characterized by inappropriate, i.e., less than or greater than normal, CCR9 functional activity. Inappropriate CCR9 functional activity might arise as the result of CCR9 expression in cells that normally do not express CCR9, increased CCR9 expression (leading to, e.g., inflammatory and immunoregulatory disorders and diseases), or decreased CCR9 expression. Inappropriate CCR9 functional activity might also arise as the result of TECK secretion by cells which normally do not secrete TECK, increased TECK expression (leading to, e.g., inflammatory and immunoregulatory disorders and diseases), or decreased TECK expression. A CCR9-mediated disorder may be completely or partially mediated by inappropriate CCR9 functional activity. A CCR9-mediated disorder is one in which modulation of CCR9 results in some effect on the underlying condition or disease (e.g., a CCR9 antagonist results in some improvement in patient well being in at least some patients).

As used herein, the phrase "effective amount" means that amount of a drug substance (i.e. the compound of the present invention) that elicits the desired biological response in a subject. Such a response includes alleviation of the symptoms of the disease or disorder being treated. The effective amount of the compound of the invention in such a therapeutic method is about 0.001 to 100 mg per kg patient body weight per day which can be administered in single or multiple doses. Preferably, the dosage level will be about 0.01 to about 25 mg/kg per day; more preferably about 0.05 to about 10 mg/kg per day. A suitable dosage level may be about 0.01 to 25 mg/kg per day, about 0.05 to 10 mg/kg per day, or about 0.1 to 5 mg/kg per day. Within this range the dosage may be 0.005 to 0.05, 0.05 to 0.5, 0.5 to 5.0, or 5.0 to 50 mg/kg per day. For oral administration, the compositions are preferably provided in the form of tablets containing 1.0 to 1000 milligrams of the active ingredient, particularly 1.0, 5.0, 10.0, 15.0, 20.0, 25.0, 50.0, 75.0, 100.0, 150.0, 200.0, 250.0, 300.0, 400.0, 500.0, 600.0, 750.0, 800.0, 900.0, and 1000.0 milligrams of the active ingredient for the symptomatic adjustment of the dosage to the patient to be treated. The compound may be administered on a regimen of 1 to 4 times per day, preferably once or twice per day.

It is to be understood, however, that the specific dose level and frequency of dosage for any particular patient may be varied and will depend upon a variety of factors including age, body weight, hereditary characteristics, general health, gender, diet, mode and time of administration, rate of excretion, drug combination, and the nature and severity of the particular condition being treated.

Administration methods include administering an effective amount of the compound or composition of the invention at different times during the course of therapy or concurrently in a combination form. The methods of the invention include all known therapeutic treatment regimens.

Diseases and conditions associated with inflammation, immune disorders, infection, and cancer may be treated or prevented with the present compound, compositions, and methods. In one group of embodiments, diseases or conditions, including chronic diseases, of humans or other species can be treated with an inhibitor of CCR9 function. These diseases or conditions include: (1) allergic diseases such as systemic anaphylaxis or hypersensitivity responses, drug allergies, insect sting allergies and food allergies, (2) inflammatory bowel diseases, such as Crohn's disease, ulcerative colitis, ileitis and enteritis, (3) vaginitis, (4) psoriasis and inflammatory dermatoses such as dermatitis, eczema, atopic dermatitis, allergic contact dermatitis, urticaria and pruritus, (5) vasculitis, (6) spondyloarthropathies, (7) scleroderma, (8) asthma and respiratory allergic diseases such as allergic asthma, allergic rhinitis, hypersensitivity lung diseases and the like, (9) autoimmune diseases, such as fibromyalagia, scleroderma, ankylosing spondylitis, juvenile RA, Still's disease, polyarticular juvenile RA, pauciarticular juvenile RA, polymyalgia rheumatica, rheumatoid arthritis, psoriatic arthritis, osteoarthritis, polyarticular arthritis, multiple sclerosis, systemic lupus erythematosus, type I diabetes, type II diabetes, glomerulonephritis, and the like, (10) graft rejection (including allograft rejection), (11) graft-v-host disease (including both acute and chronic), (12) other diseases in which undesired inflammatory responses are to be inhibited, such as atherosclerosis, myositis, neurodegenerative diseases (e.g., Alzheimer's disease), encephalitis, meningitis, hepatitis, nephritis, sepsis, sarcoidosis, allergic conjunctivitis, otitis, chronic obstructive pulmonary disease, sinusitis, Behcet's syndrome and gout, (13) pulmonary fibrosis and other fibrotic diseases, and (14) irritable bowel syndrome.

Preferably, the present methods are directed to the treatment of diseases or conditions selected from inflammatory bowel disease, including Crohn's disease and ulcerative colitis; allergic diseases such as psoriasis, atopic dermatitis, and asthma; and autoimmune diseases such as rheumatoid arthritis.

More preferably, the present methods are directed to the treatment of inflammatory bowel disease, including Crohn's disease and ulcerative colitis.

The compound and compositions of the present invention can be combined with other compounds and compositions having related utilities to prevent and treat the condition or disease of interest, such as inflammatory conditions and diseases, including inflammatory bowel disease, allergic diseases, psoriasis, atopic dermatitis and asthma, and those pathologies noted above. Selection of the appropriate agents for use in combination therapies can be made by one of ordinary skill in the art. The combination of therapeutic agents may act synergistically to effect the treatment or prevention of the various disorders. Using this approach, one may be able to achieve therapeutic efficacy with lower dosages of each agent, thus reducing the potential for adverse side effects.

The weight ratio of the compound of the present invention to the second active ingredient may be varied and will depend upon the effective dose of each ingredient. Generally, an effective dose of each will be used. Thus, for example, when a compound of the present invention is combined with an NSAID the weight ratio of the compound of the present invention to the NSAID will generally range from about 1000:1 to about 1:1000, preferably about 200:1 to about 1:200. Combinations of the compound of the present invention and other active ingredients will generally also be within the aforementioned range, but in each case, an effective dose of each active ingredient should be used.

Combination therapy includes co-administration of the compound of the invention and said other agent, sequential administration of the compound of the invention and the other agent, administration of a composition containing the compound of the invention and the other agent, or simultaneous administration of separate compositions containing the compound of the invention and the other agent.

The invention further includes the use of the compound of the invention as an active therapeutic substance, in particular in the treatment of CCR9-mediated disorders. In particular, the invention includes the use of the compound of the invention in the treatment of inflammatory bowel disease, including Crohn's disease and ulcerative colitis.

In another aspect, the invention includes the use of compounds of the invention in the manufacture of a medicament for use in the treatment of the above disorders.

The present invention is also directed to a pharmaceutical composition comprising the compound of the invention and a pharmaceutically acceptable carrier. The present invention is further directed to a method of preparing a pharmaceutical composition comprising admixing the compound of the invention and a pharmaceutically acceptable carrier.

As used herein, the phrase "pharmaceutically acceptable carrier" means any one or more compounds and/or compositions that are of sufficient purity and quality for use in the formulation of the compound of the invention that, when appropriately administered to a human, do not produce an adverse reaction, and that are used as a vehicle for a drug substance (i.e. the compound of the present invention).

The invention further includes the process for making the composition comprising mixing the compound of the invention and an optional pharmaceutically acceptable carrier; and includes those compositions resulting from such a process, which process includes conventional pharmaceutical techniques. For example, the compound of the invention may be nanomilled prior to formulation. The compound of the invention may also be prepared by grinding, micronizing or other particle size reduction methods known in the art. Such methods include, but are not limited to, those described in U.S. Pat. Nos. 4,826,689, 5,145,684, 5,298,262, 5,302,401, 5,336,507, 5,340,564, 5,346,702, 5,352,459, 5,354,560, 5,384,124, 5,429,824, 5,503,723, 5,510,118, 5,518,187, 5,518,738, 5,534,270, 5,536,508, 5,552,160, 5,560,931, 5,560,932, 5,565,188, 5,569,448, 5,571,536, 5,573,783, 5,580,579, 5,585,108, 5,587,143, 5,591,456, 5,622,938, 5,662,883, 5,665,331, 5,718,919, 5,747,001, PCT applications WO 93/25190, WO 96/24336, and WO 98/35666, each of which is incorporated herein by reference. The pharmaceutical compositions of the invention may be prepared using techniques and methods known to those skilled in the art. Some of the methods commonly used in the art are described in *Remington's Pharmaceutical Sciences* (Mack Publishing Company), the entire teachings of which are incorporated herein by reference.

The compositions of the invention include ocular, oral, nasal, transdermal, topical with or without occlusion, intravenous (both bolus and infusion), and injection (intraperitoneally, subcutaneously, intramuscularly, intratumorally, or parenterally). The composition may be in a dosage unit such as a tablet, pill, capsule, powder, granule, liposome, ion exchange resin, sterile ocular solution, or ocular delivery device (such as a contact lens and the like facilitating immediate release, timed release, or sustained release), parenteral solution or suspension, metered aerosol or liquid spray, drop, ampoule, auto-injector device, or suppository; for administration ocularly, orally, intranasally, sublingually, parenterally, or rectally, or by inhalation or insufflation.

Compositions of the invention suitable for oral administration include solid forms such as pills, tablets, caplets, capsules (each including immediate release, timed release, and sustained release formulations), granules and powders.

The oral composition is preferably formulated as a homogeneous composition, wherein the drug substance (i.e. the compound of the present invention) is dispersed evenly throughout the mixture, which may be readily subdivided into dosage units containing equal amounts of the compound of the invention. Preferably, the compositions are prepared by mixing the compound of the invention with one or more optionally present pharmaceutical carriers (such as a starch, sugar, diluent, granulating agent, lubricant, glidant, binding agent, and disintegrating agent), one or more optionally present inert pharmaceutical excipients (such as water, glycols, oils, alcohols, flavoring agents, preservatives, coloring agents, and syrup), one or more optionally present conventional tableting ingredients (such as corn starch, lactose, sucrose, sorbitol, talc, stearic acid, magnesium stearate, dicalcium phosphate, and any of a variety of gums), and an optional diluent (such as water).

Binding agents include starch, gelatin, natural sugars (e.g. glucose and beta-lactose), corn sweeteners and natural and synthetic gums (e.g. acacia and tragacanth). Disintegrating agents include starch, methyl cellulose, agar, and bentonite.

The compound of the invention may also be administered via a delayed release composition, wherein the composition includes a compound of the invention and a biodegradable slow release carrier (e.g. a polymeric carrier) or a pharmaceutically acceptable non-biodegradable slow release carrier (e.g. an ion exchange carrier).

Biodegradable and non-biodegradable delayed release carriers are well known in the art. Biodegradable carriers are used to form particles or matrices which retain a drug substance(s) (i.e. the compound of the present invention) and which slowly degrade/dissolve in a suitable environment (e.g. aqueous, acidic, basic and the like) to release the drug substance(s). Such particles degrade/dissolve in body fluids to release the drug substance(s) (i.e. compounds of the present invention) therein. The particles are preferably nanoparticles (e.g. in the range of about 1 to 500 nm in diameter, preferably about 50-200 nm in diameter, and most preferably about 100 nm in diameter). In a process for preparing a slow release composition, a slow release carrier and the compound of the invention are first dissolved or dispersed in an organic solvent. The resulting mixture is added into an aqueous solution containing an optional surface-active agent(s) to produce an emulsion. The organic solvent is then evaporated from the emulsion to provide a colloidal suspension of particles containing the slow release carrier and the compound of the invention.

Tablets and capsules represent an advantageous oral dosage unit form. Tablets may be sugarcoated or filmcoated using standard techniques. Tablets may also be coated or otherwise compounded to provide a prolonged, control-release therapeutic effect. The dosage form may comprise an inner dosage and an outer dosage component, wherein the outer component is in the form of an envelope over the inner component. The two components may further be separated by a layer which resists disintegration in the stomach (such as an enteric layer) and permits the inner component to pass intact into the duodenum or a layer which delays or sustains release. A variety of enteric and non-enteric layer or coating materials (such as polymeric acids, shellacs, acetyl alcohol, and cellulose acetate or combinations thereof) may be used.

Without further elaboration, it is believed that one skilled in the art can, using the preceding description, utilize the present invention to its fullest extent. The following Examples are, therefore, to be construed as merely illustrative and not a limitation of the scope of the present invention in any way.

Example 1

Preparation of:

4-tert-Butyl-N-[4-chloro-2-(1-oxy-pyridine-4-carbonyl)-phenyl]-benzenesulfonamide (Compound A)

A 2000 mL 3-neck round bottom flask equipped with a thermal couple, a heating mantle, a condenser, and a $N_2$ bubbler was charged with 60.0 g 4-tert-butyl-N-[4-chloro-2-(pyridine-4-carbonyl)-phenyl]-benzenesulfonamide (for a procedure for the preparation of this material see WO 2004/

046092) and 900 mL acetonitrile. 31.9 g trifluoroacetic acid was added and the reaction mixture was agitated at ambient temperature until a solution was achieved. 39.5 g urea hydrogen peroxide was added and the reaction mixture was heated to 70±5° C. for 23 hours. 63.8 g trifluoroacetic acid was added and the reaction mixture was heated to 80±5° C. to obtain a clear solution. 900 mL water was slowly added while maintaining the temperature of the reaction mixture at 70±5° C. during the addition. The reaction mixture was allowed to cool to 20±5° C. and agitated for 30 minutes. The solid precipitate was collected by filtration and the filter cake was washed with 240 mL 1:1 acetonitrile:water. The collected solid was dried under vacuum at 40±5° C. to provide 54 g of the title compound as a crystalline solid (see WO 2004/046092 for $^1$H NMR characterization data).

The X-ray powder diffraction (XRPD) pattern of this material is shown in FIG. 1 and a summary of the diffraction angles and d-spacings is given in Table I. The XRPD analysis was conducted on a PANanalytical X'Pert Pro Diffractometer, model PW3040/60, serial number DY2407 using an X'Celerator detector. The acquisition conditions included: Cu $K_\alpha$ radiation ($\lambda$=1.54059 Å), generator tension: 45 kV, generator current: 40 mA, start angle: 2.0° 2θ, end angle: 50.0° 2θ, step size: 0.0167° 2θ, time per step: 40.005 seconds. The sample was prepared using zero background (front fill) technique.

TABLE I

| Diff. Angle [°2θ] | d-spacing [Å] |
|---|---|
| 8.9301 | 9.89453 |
| 12.6165 | 7.01055 |
| 14.5957 | 6.06406 |
| 15.5479 | 5.69473 |
| 16.9374 | 5.23054 |
| 17.9034 | 4.95044 |
| 18.3833 | 4.82228 |
| 18.8783 | 4.69694 |
| 19.0236 | 4.6614 |
| 19.894 | 4.45938 |
| 21.7546 | 4.08201 |
| 21.9978 | 4.03741 |
| 23.7733 | 3.73975 |
| 24.6309 | 3.61144 |
| 26.3131 | 3.38425 |
| 27.0214 | 3.29713 |
| 27.3243 | 3.26126 |
| 32.8795 | 2.72184 |
| 36.2714 | 2.47471 |

The Raman spectrum of the title compound was recorded on a Nicolet NXR 9650 FT-Raman Spectrometer, at 4 cm$^{-1}$ resolution with excitation from a Nd:YVO4 laser ($\lambda$=1064 nm). The Raman spectrum of this material is shown in FIG. 4 with major peaks observed at 657, 671, 749, 784, 964, 1086, 1110, 1149, 1180, 1229, 1270, 1487, 1594, 1609, and 1676 cm$^{-1}$.

Example 2

Preparation of:

An anhydrous crystalline sodium salt of 4-tert-butyl-N-[4-chloro-2-(1-oxy-pyridine-4-carbonyl)-phenyl]-benzenesulfonamide (Compound B—anhydrous crystalline form)

A reaction vessel was charged with 300 g 4-tert-butyl-N-[4-chloro-2-(1-oxy-pyridine-4-carbonyl)-phenyl]-benzenesulfonamide, 4,737 mL Industrial Methylated Spirits (IMS), and 302.4 mL water. 27.245 g sodium hydroxide pellets were added to the slurry at 25° C. The reaction mixture was agitated at ambient temperature for 50 minutes, followed by heating to ~78° C. to dissolve all solids. The clear solution was then filtered while maintaining the temperature above 55° C. throughout the filtration process. After filtration, the filtered solution was reheated to 75° C. and then cooled to 55° C. and seeded with 3.0 g Compound B—anhydrous crystalline form (prepared by an analogous smaller-scale procedure absent seeding) as a slurry in 15 mL IMS at ambient temperature. The slurry was held at 55° C. overnight and then cooled to 45° C. Vacuum distillation was employed while heating the reactor jacket to 65° C. and not allowing the slurry temperature to exceed 55° C., leaving ~1,500 mL of slurry in the reactor. The slurry was cooled to −10° C., held at that temperature overnight, and then transferred to a filter dryer and settled for 10 minutes. The jacket temperature of the filter was pre-chilled to −10° C. The mother liquors were removed to break-through using 0.5 to 1 bar nitrogen pressure. The crystallizer was charged with a first pre-chilled wash of 1,200 mL IMS, chilled to −10° C. The wash was transferred to the cake in the filter, agitated for 10 minutes, settled for 10 minutes, and removed under 0.5 to 1 bar nitrogen pressure. The washing of the filter cake was repeated two additional times under the same conditions. The jacket temperature of the filter was increased to 20° C. and the cake was blown-down under 0.5 to 1 bar nitrogen pressure until the solvent being removed was reduced to a trickle. The wet cake was dried at 70° C. with agitation under vacuum to provide 258.3 g of the title compound as a yellow crystalline solid.

The X-ray powder diffraction (XRPD) pattern of this material is shown in FIG. 3 and a summary of the diffraction angles and d-spacings is given in Table II. The XRPD analysis was conducted on a PANanalytical X'Pert Pro Diffractometer, model PW3040/60, serial number DY2407 using an X'Celerator detector. The acquisition conditions included: Cu $K_\alpha$ radiation ($\lambda$=1.54059 Å), generator tension: 45 kV, generator current: 40 mA, start angle: 2.0° 2θ, end angle: 50.0° 2θ, step size: 0.0167° 2θ, time per step: 40.005 seconds. The sample was prepared using zero background (front fill) technique.

TABLE II

| Diff. Angle [°2θ] | d-spacing [Å] |
|---|---|
| 4.7052 | 18.76531 |
| 9.0615 | 9.75138 |
| 12.0211 | 7.35641 |
| 14.2498 | 6.21047 |
| 17.7364 | 4.99669 |
| 18.0898 | 4.89985 |
| 19.1712 | 4.62583 |
| 19.7582 | 4.48971 |
| 20.1043 | 4.4132 |
| 21.3099 | 4.16617 |
| 22.4826 | 3.95145 |
| 24.2524 | 3.66694 |
| 27.0057 | 3.29901 |
| 27.1831 | 3.27789 |
| 27.6689 | 3.22142 |
| 28.6061 | 3.11798 |
| 28.773 | 3.10027 |
| 28.9712 | 3.07952 |
| 30.1157 | 2.96504 |
| 31.6334 | 2.82616 |
| 33.4936 | 2.67332 |
| 33.6372 | 2.66224 |
| 37.5548 | 2.39303 |

The Raman spectrum of the title compound was recorded on a Nicolet NXR 9650 FT-Raman Spectrometer, at 4 cm$^{-1}$ resolution with excitation from a Nd:YVO4 laser (λ=1064 nm). The Raman spectrum of this material is shown in FIG. 6 with major peaks observed at 601, 632, 651, 664, 726, 740, 803, 853, 931, 1080, 1123, 1138, 1162, 1318, 1395, 1458, 1526, 1595, 1614, and 1647 cm$^{-1}$.

The differential scanning calorimetry (DSC) thermogram of the title compound was recorded on a TA Instruments Q1000 Differential Scanning calorimeter and is shown in FIG. 8. The sample was weighed into an aluminium pan, a pan lid placed on top and lightly crimped without sealing the pan. The experiments were conducted using a heating rate of 15° C./min. The DSC thermogram of Compound B—anhydrous crystalline form exhibits an endotherm with an onset temperature at about 310° C. A person skilled in the art would recognize that the onset temperature of the endotherm may vary depending on the experimental conditions.

The thermogravimetric analysis (TGA) thermogram of the title compound was recorded on a TA Instruments Q5000 Themrogravimetric Analyzer and is shown in FIG. 10. The experiments were conducted using a heating rate of 15° C./min. The TGA thermogram of Compound B—anhydrous crystalline form exhibits negligible weight loss up to 300° C.

Example 3

Preparation of:

The amorphous sodium salt of 4-tert-butyl-N-[4-chloro-2-(1-oxy-pyridine-4-carbonyl)-phenyl]-benzenesulfonamide (Compound B—amorphous form)

The anhydrous crystalline sodium salt of 4-tert-butyl-N-[4-chloro-2-(1-oxy-pyridine-4-carbonyl)-phenyl]-benzenesulfonamide (500 mg) was placed into a 10 mL stainless steel jar containing two grinding balls, 7 mm in diameter. The sample was ground at ambient temperature for 30 minutes at a frequency of 30 Hz using a Retsch Mill MM301 Apparatus.

The X-ray powder diffraction (XRPD) pattern of this material is shown in FIG. 2. The XRPD analysis was conducted on a PANanalytical X'Pert Pro Diffractometer, model PW3040/60, serial number DY2407 using an X'Celerator detector. The acquisition conditions included: Cu K$_\alpha$ radiation (λ=1.54059 Å), generator tension: 45 kV, generator current: 40 mA, start angle: 2.0° 2θ, end angle: 50.0° 2θ, step size: 0.0167° 2θ, time per step: 40.005 seconds. The sample was prepared using zero background (front fill) technique.

Figure 5:
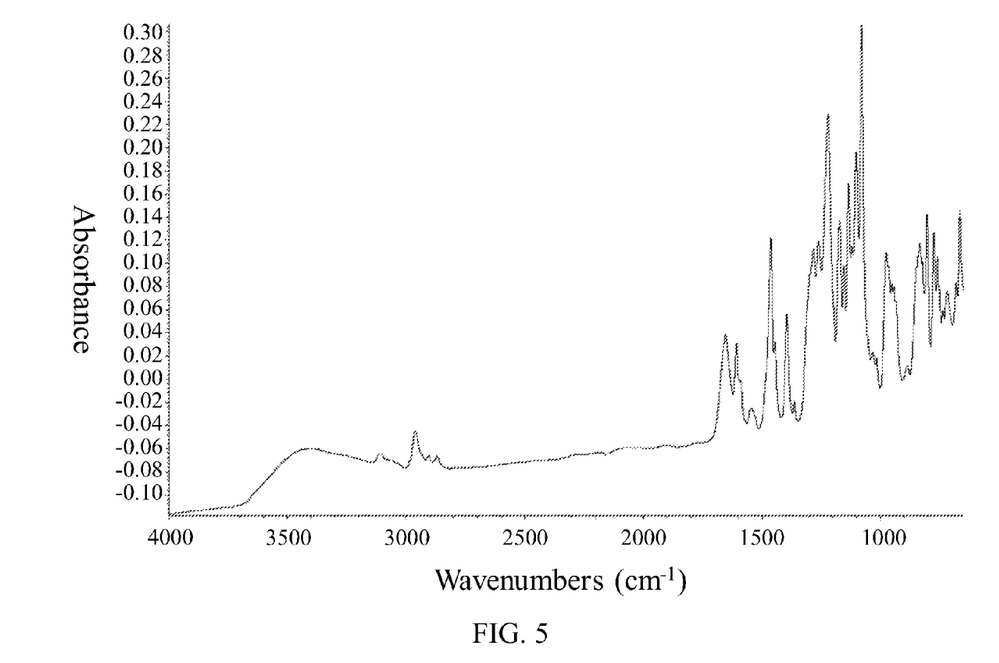
FIG. 5 shows a Fourier transform infrared spectrum of Compound B—amorphous form.

The Fourier transform infrared (FT-IR) spectrum of the title compound is shown in FIG. 5 with major peaks observed at 718, 159, 775, 803, 833, 975, 1078, 1102, 1134, 1154, 1172, 1219, 1261, 1283, 1394, 1460, 1608, and 1654 cm$^{-1}$.

Figure 7:
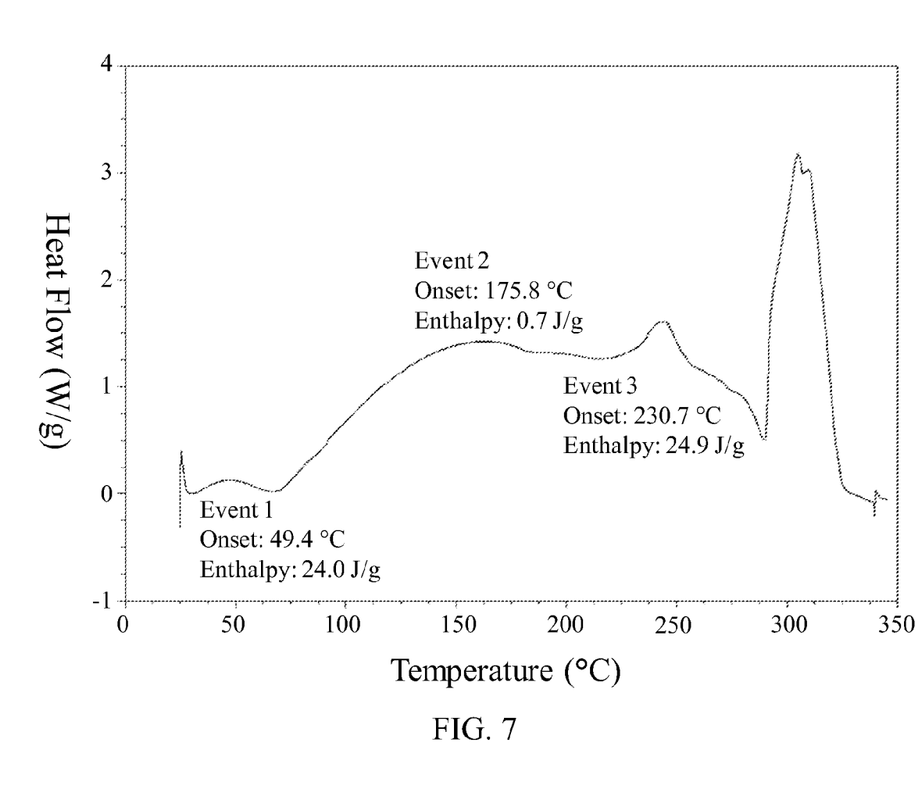
FIG. 7 shows a differential scanning calorimetry trace of Compound B—amorphous form.

The differential scanning calorimetry (DSC) thermogram of the title compound was recorded on a TA Instruments Q1000 Differential Scanning calorimeter and is shown in FIG. 7. The sample was weighed into an aluminium pan, a pan lid placed on top and lightly crimped without sealing the pan. The experiments were conducted using a heating rate of 15° C./min.

Figure 9:
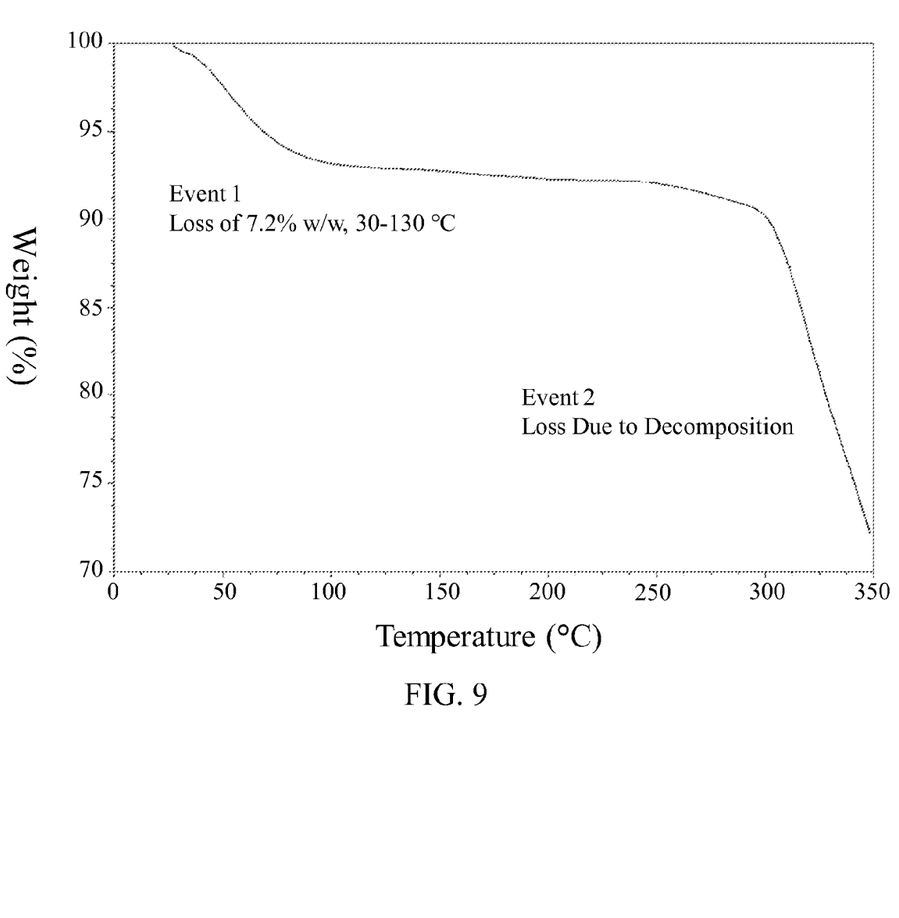
FIG. 9 shows a thermogravimetric analysis trace of Compound B—amorphous form.

The thermogravimetric analysis (TGA) thermogram of the title compound was recorded on a TA Instruments Q5000 Themrogravimetric Analyzer and is shown in FIG. 9. The experiments were conducted using a heating rate of 15° C./min.

What is claimed is:

1. A crystalline form of anhydrous sodium salt of 4-tert-butyl-N-[4-chloro-2-(1-oxy-pyridine-4-carbonyl)-phenyl]-benzenesulfonamide is characterized by an X-ray powder diffraction pattern comprising at least three diffraction angles, when measured using Cu K$_\alpha$ radiation, selected from the group consisting of: 4.7, 9.1, 12.0, 14.2, 17.7, 18.1, 19.2, 19.8, 20.1, 21.3, 22.5, 24.3, 27.0, 27.2, 27.7, 28.6, 28.8, 29.0, 30.1, 31.6, 33.5, 33.6, and 37.6 degrees 2θ±0.2 degrees 2θ.

2. The crystalline form of claim 1, wherein the crystalline form is characterized by an X-ray powder diffraction pattern comprising at least three diffraction angles selected from the group consisting of: 4.7, 9.1, 12.0, 14.2, 18.1, 19.2, 19.8, 20.1, 21.3, 22.5, 24.3, 27.2, 28.8, and 37.6 degrees 2θ±0.2 degrees 2θ.

3. The crystalline form of claim 1, wherein the crystalline form is characterized by an X-ray powder diffraction pattern comprising at least three diffraction angles selected from the group consisting of: 4.7, 12.0, 14.2, 18.1, 19.2, and 24.3 degrees 2θ±0.2 degrees 2θ.

4. The crystalline form of claim 1, wherein the crystalline form is characterized by an X-ray powder diffraction pattern substantially in accordance with FIG. 3.

5. The crystalline form of claim 1, wherein the crystalline form is characterized by a Raman spectrum comprising at least three peaks at positions selected from the group consisting of: 601, 632, 651, 664, 726, 740, 803, 853, 931, 1080, 1123, 1138, 1162, 1318, 1395, 1458, 1526, 1595, 1614, and 1647 cm$^{-1}$±4 cm$^{-1}$.

6. The crystalline form of claim 5, wherein the crystalline form is characterized by a Raman spectrum comprising at least three peaks at positions selected from the group consisting of: 664, 740, 803, 853, 1080, 1123, 1162, 1318, 1458, 1526, 1595, 1614, and 1647 cm$^{-1}$±4 cm$^{-1}$.

7. The crystalline form of claim 5, wherein the crystalline form is characterized by a Raman spectrum comprising at least three peaks at positions selected from the group consisting of: 664, 1162, 1458, 1614, and 1647 cm$^{-1}$±4 cm$^{-1}$.

8. The crystalline form of claim 5, wherein the crystalline form is characterized by a Raman spectrum comprising at least three peaks at positions selected from the group consisting of 664, 740, 803, 853, 1080, 1123, 1162, 1318, 1458, 1526, 1595, 1614, and 1647 cm$^{-1}$±4 cm$^{-1}$.

9. The crystalline form of claim 1, wherein said crystalline form is characterized by a Raman spectrum substantially in accordance with FIG. 6.

10. The crystalline form of claim 1, wherein the crystalline form differential scanning calorimetry themogram profile is substantially in accordance with FIG. 8.

11. The crystalline form of claim 1, wherein the crystalline form thermogravimetric analysis trace is substantially in accordance with FIG. 10.

12. A pharmaceutical composition comprising the crystalline form according to claim 1 and a pharmaceutically acceptable carrier.

13. The composition of claim 12 wherein the composition is adapted for oral administration.

14. The composition of claim 12 wherein the composition is in a form of a tablet or capsule.

15. A method of treating a CCR9-mediated disorder in a subject in need thereof comprising administering to the subject an effective amount of the crystalline form of claim 1.

16. The method of claim 15 wherein the CCR9-mediated disorder is an inflammatory bowel disease.

17. The method of claim 16 wherein the inflammatory bowel disease is selected from Crohn's disease and ulcerative colitis.

* * * * *